US008425510B2

(12) United States Patent
Yamamoto et al.

(10) Patent No.: US 8,425,510 B2
(45) Date of Patent: Apr. 23, 2013

(54) TREATMENT INSTRUMENT FOR ENDOSCOPE INCLUDING A SHEATH HAVING A TAPERED PORTION AT A DISTAL END PORTION THEREOF

(75) Inventors: Hironori Yamamoto, Shimotsuke (JP); Ryo Ishikawa, Saitama (JP)

(73) Assignees: Jichi Medical University, Tochighi (JP); Fujifilm Corporation, Tokyo (JP)

( * ) Notice: Subject to any disclaimer, the term of this patent is extended or adjusted under 35 U.S.C. 154(b) by 700 days.

(21) Appl. No.: 12/569,774

(22) Filed: Sep. 29, 2009

(65) Prior Publication Data

US 2010/0081872 A1 Apr. 1, 2010

(30) Foreign Application Priority Data

Sep. 30, 2008 (JP) .................................. 2008-255016

(51) Int. Cl.
*A61B 18/18* (2006.01)
(52) U.S. Cl.
USPC .................................. 606/46; 606/41; 606/45
(58) Field of Classification Search ............... 606/40–45
See application file for complete search history.

(56) References Cited

U.S. PATENT DOCUMENTS

| 5,085,659 | A * | 2/1992 | Rydell | 606/47 |
| 5,171,255 | A | 12/1992 | Rydell | |
| 7,371,236 | B2 * | 5/2008 | Okada | 606/45 |
| 7,618,416 | B2 * | 11/2009 | Ono et al. | 606/45 |
| 7,658,738 | B2 * | 2/2010 | Nobis et al. | 606/45 |
| 2004/0167514 | A1 * | 8/2004 | Okada | 606/45 |
| 2005/0072280 | A1 | 4/2005 | Ono et al. | |
| 2007/0016184 | A1 * | 1/2007 | Cropper et al. | 606/41 |
| 2009/0254085 | A1 * | 10/2009 | Yamamoto | 606/46 |

FOREIGN PATENT DOCUMENTS

| EP | 1 522 269 A1 | 4/2005 |
| EP | 1 943 972 A1 | 7/2008 |
| EP | 2 057 953 A1 | 5/2009 |
| JP | 3655664 | 3/2005 |
| WO | WO 2007/034708 A1 | 3/2007 |
| WO | WO 2008/026689 A1 | 6/2008 |

OTHER PUBLICATIONS

European Search Report dated Dec. 10, 2009.
Chinese Office Action dated Oct. 9, 2012, with English translation.

* cited by examiner

*Primary Examiner* — Linda Dvorak
*Assistant Examiner* — Amanda Scott
(74) *Attorney, Agent, or Firm* — McGinn IP Law Group, PLLC

(57) ABSTRACT

A treatment instrument for an endoscope includes: an operation portion; a cylindrical sheath that is connected to the operation portion and that also comprises an insertion portion; an axial electrode that is protruded from and retracted into a distal end opening portion of the sheath by an operation of the operation portion; and a distal end electrode portion that is provided at a distal end portion of the axial electrode; wherein a tapered portion is formed at a distal end portion of the sheath, the tapered portion being in a tapered shape that a distal end side of the distal end portion is narrower than a proximal end side of the distal end portion.

11 Claims, 13 Drawing Sheets

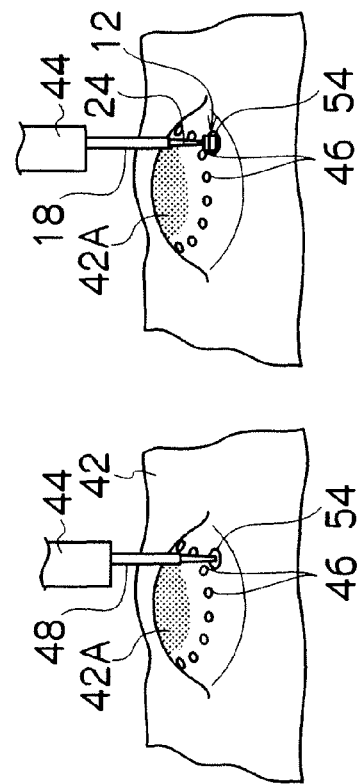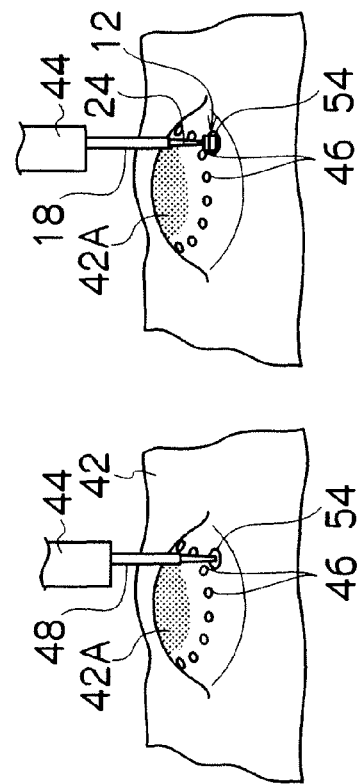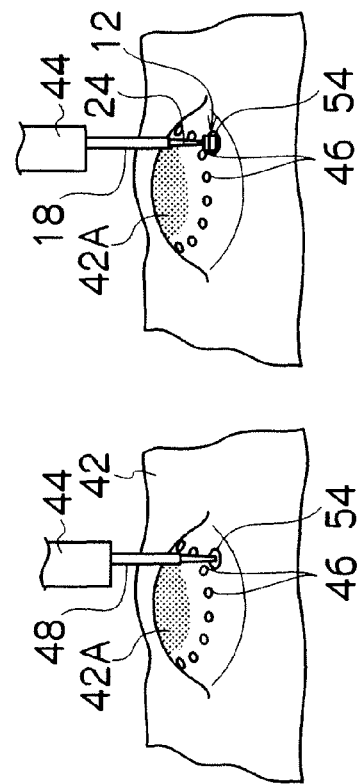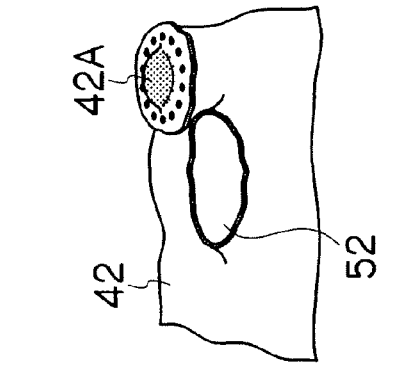
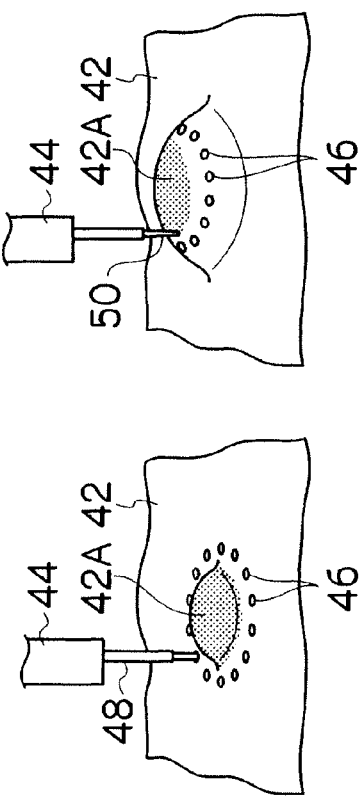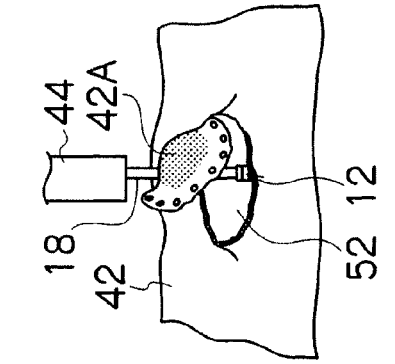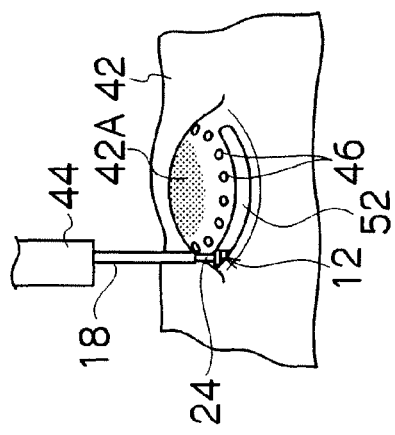

TREATMENT INSTRUMENT FOR ENDOSCOPE INCLUDING A SHEATH HAVING A TAPERED PORTION AT A DISTAL END PORTION THEREOF

BACKGROUND OF THE INVENTION

1. Field of the Invention

The present invention relates to a treatment instrument for an endoscope, and more particularly to a treatment instrument for an endoscope that is used in endoscopic submucosal dissection (ESD).

2. Description of the Related Art

Endoscopic mucosal resection is recognized as a minimally invasive and reliable treatment that is useful as a radical operation for neoplastic mucosal lesions such as early esophageal cancer, early gastric cancer and early colorectal cancer. In recent years, a method referred to as endoscopic submucosal dissection (ESD) has been developed and brought into widespread use as a method that applies endoscopic mucosal resection to enable reliable en bloc resection of a lesion that extends over a wider area. In this method, en bloc resection of neoplastic mucosa is performed by cleaving submucosa between the mucosa and muscularis propria, after dissection of peritumoral mucosa.

International Patent Publication Nos. WO 2007/034708 A1 and WO 2008/026689 A1 disclose a treatment instrument for an endoscope that is used for endoscopic submucosal dissection (ESD).

A treatment instrument for an endoscope disclosed in FIG. 1 of International Patent Publication No. WO 2007/034708 A1 comprises a hand-side operation portion and an insertion portion that is connected to the hand-side operation portion. The insertion portion comprises a non-conductive cylindrical flexible sheath, an conductive wire that is passed through inside of the sheath, and a distal end electrode portion that is attached to a distal end portion of the sheath and is connected to a distal end portion of the wire. A proximal end portion of the wire is connected to a connector provided in the hand-side operation portion, and the connector is connected to a high-frequency current supply device.

Further, a treatment instrument for an endoscope disclosed in FIG. 28 of International Patent Publication No. WO 2008/026689 A1 comprises a hand-side operation portion and an insertion portion that is connected to the hand-side operation portion. The insertion portion comprises a non-conductive cylindrical flexible sheath, an conductive wire that is passed through inside of the sheath, an axial electrode that is protruded from or retracted into the distal end portion of the sheath by an operation of the hand-side operation portion and is connected to the distal end portion of the wire, and a distal end electrode portion that is connected to the distal end portion of the axial electrode. The proximal end portion of the wire is connected to a connector provided in the hand-side operation portion, and a high-frequency current supply device is connected to the connector.

Each of the aforementioned treatment instruments for an endoscope is inserted into a forceps channel that is arranged so as to pass through the endoscope insertion portion, and a distal end portion of the sheath protrudes from a forceps opening formed in a distal end rigid portion of the endoscope insertion portion. A surgeon operates the hand-side operation portion while observing an image from an image pickup portion provided at the distal end rigid portion to operate the distal end electrode portion to resect mucosa at a treatment site. Further, the treatment instrument for an endoscope disclosed in International Patent Publication No. WO 2008/026689 A1 can also dissect mucosa using the axial electrode by passing a high frequency current to the axial electrode.

SUMMARY OF THE INVENTION

The sheath of the treatment instruments for an endoscope described in International Patent Publication Nos. WO 2007/034708 A1 and WO 2008/026689 A1 is simply a cylindrical shape in which the distal end portion has the same external dimensions as the other portions. Consequently, an image of the distal end portion of the sheath occupies a large area of an observation image that is transmitted from the image pickup portion of the endoscope. Thus, there is the drawback that visibility with respect to the distal end electrode portion and the axial electrode that are on an extension of the distal end portion of the sheath as well as a treatment site is poor. Also, there is the drawback that it is difficult to insert the distal end electrode portion into the submucosa from the dissected mucosa.

The present invention has been made in consideration of these circumstances, and an object of this invention is to provide a treatment instrument for an endoscope that can improve visibility with respect to a distal end electrode portion, an axial electrode, and a treatment site, and with which ablation of mucosa or submucosa can be safely and easily performed.

To achieve the foregoing object, the first aspect of the present invention provides a treatment instrument for an endoscope including: a treatment instrument for an endoscope, comprising: an operation portion; a cylindrical sheath that is connected to the operation portion and that also comprises an insertion portion; an axial electrode that is protruded from and retracted into a distal end opening portion of the sheath by an operation of the operation portion; and a distal end electrode portion that is provided at a distal end portion of the axial electrode; wherein a distal end portion of the sheath includes a tapered portion, the tapered portion being formed in a tapered shape that a distal end side of the distal end portion is narrower than a proximal end side of the distal end portion.

According to the first aspect of the present invention, since the distal end portion of the sheath is formed in a tapered shape, a part of the distal end portion of the sheath that appears in an observation image becomes reduced in size. Therefore, it is possible to observe the distal end electrode portion, the axial electrode, and a treatment site that can not be observed according to the conventional art since observation thereof is hindered by the distal end portion of the sheath. Therefore, according to the treatment instrument for an endoscope of the first aspect of the present invention, visibility with respect to the distal end electrode portion, the axial electrode, and the treatment site can be improved, and ablation of mucosa or submucosa can also be performed safely and easily.

The second aspect of the present invention provides the treatment instrument for an endoscope according to the first aspect, wherein the tapered portion of the distal end portion of the sheath is formed in a tapered shape with a continuous surface, or in a shape that is tapered in a stepwise fashion. The term "continuous surface" of the tapered portion also includes a surface having a cross section formed in a linear shape and a surface having a cross section formed in an arcuate shape. Further, the term "surface in a shape that is tapered in a stepwise fashion" refers to a surface having a cross section formed in a stepped shape. More specifically, a tapered portion of the second aspect includes all shapes that are formed in a tapered shape.

Further, the third aspect of the present invention provides the treatment instrument for an endoscope according to the first or the second aspect, wherein the tapered portion of the distal end portion of the sheath is composed by an insulative member that is a separate element to the sheath, and the insulative member is attached to the distal end opening portion of the sheath. For instance, the tapered portion is formed by an insulative member that is a separate element to the sheath. The insulative member is for example a ceramic with a high degree of rigidity. And, the axial electrode is slidably supported in a through-hole formed in the ceramic. In this instance, a protrusion/retraction operation of a rod-shaped member can be stable. Also, wobbling of the axial electrode or the distal end electrode at a time of dissection or resection is suppressed. Therefore, operability of the treatment instrument for an endoscope is improved.

Furthermore, the fourth aspect of the present invention provides the treatment instrument for an endoscope according to any one of the first to the third aspect, wherein the distal end electrode portion includes: a conductive portion; and non-conductive portions which is provided on a distal end side and a proximal end side of the conductive portion, and sandwiches the conductive portion, wherein the conductive portion exposes in a band shape on a lateral face of the distal end electrode portion. According to the fourth aspect, a side face of the distal end electrode portion has a sandwich structure in which a band-shaped conductive portion is sandwiched by non-conductive portions. Thus, when the distal end of the distal end electrode portion is contacted against muscularis propria, the non-conductive portion contacts against the muscularis propria and the conductive portion does not contact against the muscularis propria. Therefore, according to the distal end electrode portion of the fourth aspect, cleaving of muscularis propria can be reliably prevented. Further, according to the distal end electrode portion of the fourth aspect, when the distal end electrode portion is moved laterally, the side face of the distal end electrode portion contacts against submucosa, and then the submucosa against which the band-shaped conductive portion contacts is cleaved. Therefore, according to the distal end electrode portion of the fourth aspect, the submucosa can be cleaved without damaging the muscularis propria.

Furthermore, the fifth aspect of the present invention provides the treatment instrument for an endoscope according to any one of the first to the third aspect, wherein the distal end electrode portion comprises: an non-conductive portion that is formed in a cross shape; and conductive portions that are provided at a distal end side and a proximal end side of the non-conductive portion.

Further, the sixth aspect of the present invention provides the treatment instrument for an endoscope according to any one of the first to the fifth aspect, wherein the tapered portion of the distal end portion of the sheath is formed to satisfy condition indicated by expressions: $0.5a \leq b \leq 1.5a$, $0.4c \leq d \leq 0.6c$, and $d < b$, where a length in an axial direction of the distal end electrode portion is denoted by "a", a length in an axial direction of the tapered portion is denoted by "b", external dimensions on a proximal end side of the tapered portion are denoted by "c", and external dimensions on a distal end side of the tapered portion are denoted by "d".

When the length in the axial direction of the tapered portion "b" is less than 0.5a, the field of view can not be gotten, and it is also difficult to slip the distal end electrode portion into submucosa from ablated mucosa. Further, when the length in the axial direction of the tapered portion "b" is larger than 1.5a, since the tapered portion is too long, the length of the axial electrode (retracted state) positioned inside the sheath also lengthens, and the length of a rigid section (guide portion of the axial electrode) at the distal end of the sheath lengthens. As a result, the insertability of the treatment instrument for an endoscope into the forceps channel deteriorates.

With regard to the external dimensions "d" on the distal end side of the tapered portion, the external dimensions "d" should ideally be close to the diameter of the axial electrode. Since the external dimensions "d" are too small when they are less than 0.4c, the diameter of the axial electrode also narrows. Thus, there is a risk that the axial electrode breaks. Further, in this case, since the distal end of the tapered portion or the axial electrode become too sharp, there is a risk of damaging the mucosa or submucosa. Furthermore, since the distal end contacts against a proximal end of the distal end electrode portion when the axial electrode portion is in a retracted state, the stability of the distal end electrode portion deteriorates. When the external dimensions "d" on the distal end side of the tapered portion is larger than 0.6c, the angle of the tapered portion becomes obtuse, and the field of view can not be gotten since the tapered portion becomes approximately a circular cylindrical shape.

According to the treatment instrument for an endoscope of the aspects of the present invention, since a distal end portion of a sheath is formed in a tapered shape, visibility with respect to a distal end electrode portion, an axial electrode, and a treatment site can be improved, and ablation of mucosa or submucosa can be performed safely and with ease.

BRIEF DESCRIPTION OF THE DRAWINGS

FIGS. 4A to 4G are views that illustrate a method of performing an endoscopic submucosal dissection using the treatment instrument for an endoscope shown in FIG. 1;

DETAILED DESCRIPTION OF THE PREFERRED EMBODIMENTS

Hereunder, preferred embodiments of a treatment instrument for an endoscope relating to the present invention are described in detail in accordance with the attached drawings.

Figure 1:
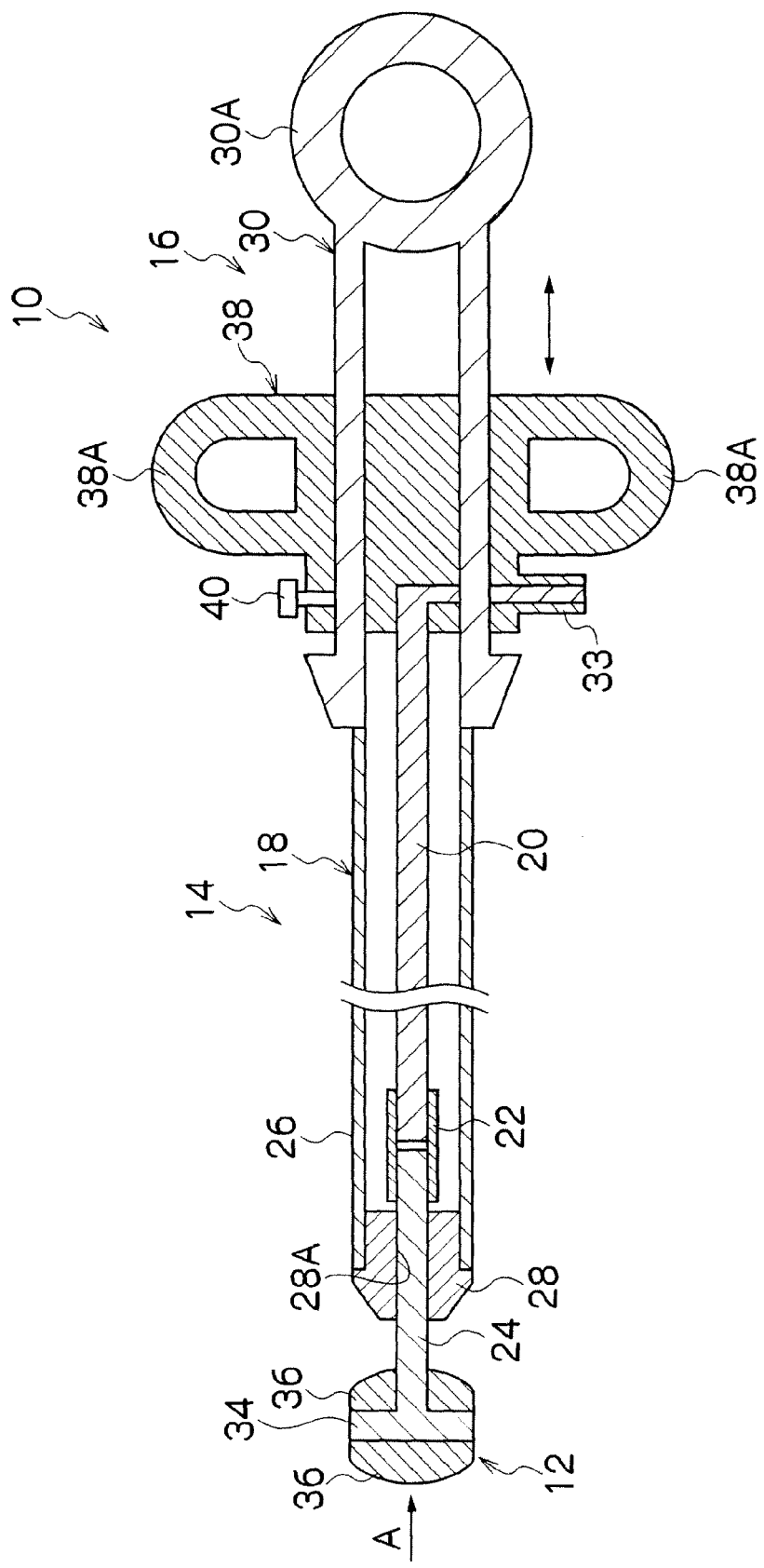
FIG. 1 is a cross-sectional view that illustrates a treatment instrument for an endoscope according to the first embodiments of the present invention.
Figure 2:
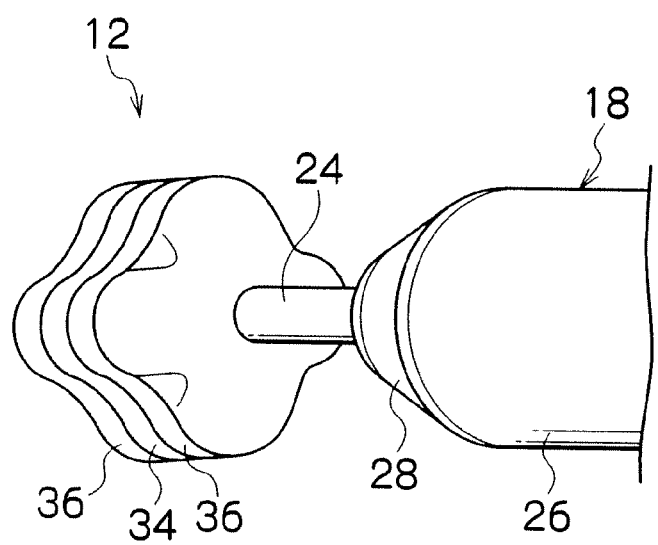
FIG. 2 is an enlarged oblique perspective view that illustrates the configuration of a distal end electrode portion of the treatment instrument for an endoscope shown in FIG. 1.

FIG. 1 is a cross-sectional view that illustrates a treatment instrument 10 for an endoscope according to the first embodiments. FIG. 2 is an enlarged oblique perspective view that illustrates the configuration of a distal end electrode portion 12 shown in FIG. 1.

As shown in FIG. 1, the treatment instrument 10 for an endoscope includes an insertion portion 14 that is inserted inside the body, and a hand-side operation portion 16 that is connected with the insertion portion 14. When using the treatment instrument 10 for an endoscope, the hand-side operation portion 16 is grasped by a surgeon, and the insertion portion 14 is inserted into and withdrawn from a forceps channel (not shown) of an endoscope.

The insertion portion 14 includes a non-conductive sheath 18, an conductive wire 20 that is passed through the inside of the sheath 18, an axial electrode 24 that is fixed to a distal end of the wire 20 via a connection pipe 22, and a distal end electrode portion 12 that is provided at the distal end of the axial electrode 24.

Figure 3:
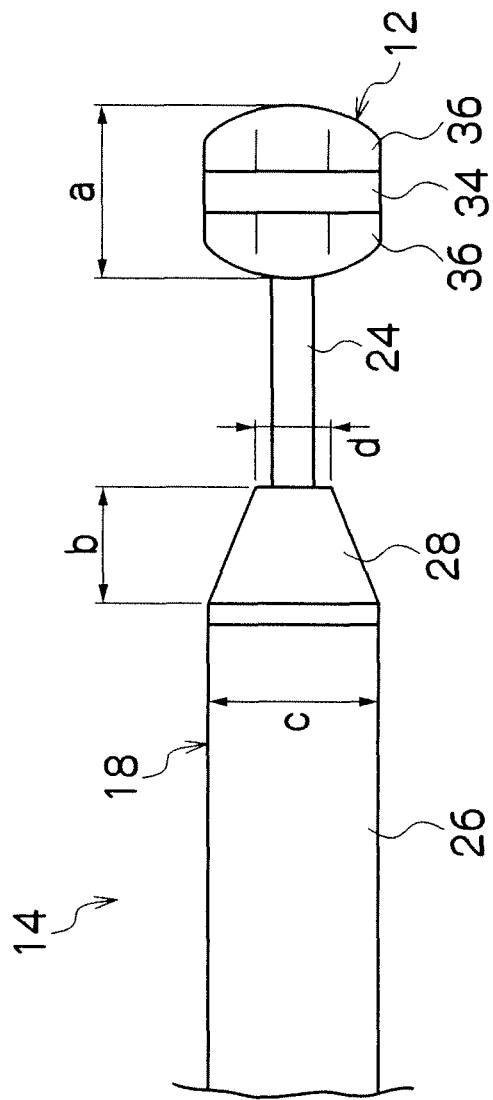
FIG. 3 is a side view of the treatment instrument for an endoscope shown in FIG. 1.

As shown in FIG. 3, the sheath 18 includes a flexible cylindrical tube 26 and a rigid collar member 28 that is fixed to a distal end opening portion of the tube 26. A proximal end portion of the tube 26 is connected to a main unit 30 of the hand-side operation portion 16. The collar member 28 is made from a hard material (for example, a ceramic) that is adiathermic (thermally-insulative) and non-conductive (electrically-insulative), and is formed in a substantially cylindrical shape with an inner diameter that is somewhat larger than the outer diameter of the axial electrode 24. The inner portion with the inner diameter serves as a through-hole 28A (see FIG. 1) that allows the axial electrode 24 to protrude and retract. The axial electrode 24 is passed through the through-hole 28A, and the axial electrode 24 is stably guided by the collar member 28. Thus, the distal end electrode portion 12 stretches straight, and wobbling of the axial electrode 24 or the distal end electrode portion 12 reduces. Further, by providing the adiathermic collar member 28 between the tube 26 and the axial electrode 24. Therefore, it is possible to prevent heat of the axial electrode 24 from being transmitted to the tube 26 so that thermal effects on the tube 26 can be eliminated.

An exposed portion of the collar member 28 is exposed from the distal end of the sheath 18, and is formed in a substantially conical shape. The surface of the exposed portion of the collar member 28 is formed as a tapered face, and the diameter of the distal end side of the exposed portion is smaller than the diameter of the proximal end side (the tube side) of the exposed portion. The tapered face of the collar member 28 is described later. The collar member 28 also fulfills a function of regulating a protruding amount (advancing amount) of the distal end electrode portion 12. When the distal end electrode portion 12 is advanced with respect to the sheath 18, the connection pipe 22 contacts against the collar member 28. Thus, the advance of the distal end electrode portion 12 is regulated by the collar member 28.

The wire 20 is inserted through the inside of the tube 26 of the sheath 18. A proximal end portion of the wire 20 is connected to the connector 33 of the hand-side operation portion 16. A high-frequency current supply device (not shown) is connected to the connector 33, and a high frequency current from the high-frequency current supply device is supplied to the wire 20.

A distal end of the wire 20 is fitted into the conductive connection pipe 22 from the proximal end side of the connection pipe 22. And, the wire 20 is fixed to the connection pipe 22 by welding or brazing or the like. The conductive axial electrode 24 is fitted into the distal end side of the connection pipe 22, and is also fixed to the connection pipe 22 by welding or brazing or the like. Thus, the wire 20 and the axial electrode 24 are connected via the connection pipe 22.

The distal end electrode portion 12 is provided at the distal end of the axial electrode 24. The distal end electrode portion 12 is formed in a substantially gear-wheel shape when viewed from the front side (direction of arrow "A" in FIG. 1). More specifically, as shown in FIG. 2, four protruded portions and four depressed portions are alternately disposed on the distal end electrode portion 12 circumferentially. The peaks of the protruded portions are made round, and the protruded portions are formed with a curvature such that the distal ends do not cleave muscularis propria 32 even when the distal ends push against the muscularis propria 32 described later (see FIG. 5). The number of protruded portions and depressed portions of the distal end electrode portion 12 is not limited to four, and may be three or less, or five or more.

The distal end electrode portion 12 shown in FIG. 2 is formed in a sandwich structure in which an conductive portion 34 which is a metal plate or the like is sandwiched between a pair of non-conductive portions (insulated portions) 36 and 36 which is an non-conductive material such as a ceramic or plastic. The conductive portion 34 and non-conductive portions 36 are formed in the same gear-wheel shape as viewed from the front side, and the lateral faces of the conductive portion 34 and the non-conductive portions 36 and 36 become even when the conductive portion 34 and the non-conductive portions 36 and 36 are superimposed. Accordingly, the conductive portion 34 is exposed so as to go round the side face of the distal end electrode portion 12 like a band. The non-conductive portions 36 and 36 are provided at the distal end side and the proximal end side of the distal end electrode portion 12.

The non-conductive portion 36 on the distal end side and the non-conductive portion 36 on the proximal end side are formed in substantially the same shape. A center part of the distal end side surface of the non-conductive portion 36 on the distal end side protrudes in a rounded fashion to the distal end side and a center part of the proximal end surface of the non-conductive portion 36 on the proximal end side protrudes in a rounded fashion to the proximal end side, so that the entire distal end electrode portion 12 is formed in a substantially spherical shape. By providing the non-conductive portion 36 on the distal end side with a degree of roundness, friction between the non-conductive portion 36 on the distal end side and the muscularis propria 32 (see FIG. 5) reduces, and hence the distal end electrode portion 12 can be moved smoothly even in a state in which the non-conductive portion 36 is pushed against the muscularis propria 32.

The conductive portion 34 is integrally formed in the axial electrode 24, and the conductive portion 34 is connected to the wire 20 shown in FIG. 1. Accordingly, by operating the aforementioned high-frequency current supply device (not shown), a high frequency current can be made to flow to the conductive portion 34. The conductive portion 34 and the axial electrode 24 may be integrated. The conductive portion 34 and the axial electrode 24 may also be provided as separate members. A configuration may also be adopted in which the conductive portion 34 and the axial electrode 24 are connected in a separate manner to the high-frequency current supply device, and a high frequency current is selectively supplied to the conductive portion 34 and the axial electrode 24 by the high-frequency current supply device.

The hand-side operation portion 16 includes a main unit 30 and a slider 38. A finger engagement portion 30A for engaging a thumb of the surgeon is formed in a ring shape at a proximal end portion of the main unit 30. The slider 38 is slidably supported by the main unit 30. A locking screw 40 provided in the slider 38 is operated to perform locking and unlocking between the slider 38 and the main unit 30. Finger engagement portions 38A and 38A for engaging an index finger and a middle finger of the surgeon are also formed in a ring shape in the slider 38.

The proximal end portion of the tube 26 of the sheath 18 is fixed to the distal end of the main unit 30. The proximal end portion of the wire 20 is fixed to the distal end of the slider 38. Accordingly, by sliding the slider 38 with respect to the main unit 30, the wire 20, the axial electrode 24 and the distal end electrode portion 12 are advanced or retreated with respect to the sheath 18.

By sliding the slider 38 forward with respect to the main unit 30, the axial electrode 24 protrudes from the distal end of the sheath 18 (the collar member 28), and enters an exposed state. Accordingly, by passing a high frequency current to the axial electrode 24 in the exposed state, cleavage or dissection of mucosa 42 (see FIG. 4E) can be performed by the axial electrode 24 in the exposed state.

Further, by sliding the slider 38 rearward with respect to the main unit 30, the proximal end of the distal end electrode portion 12 contacts against the distal end of the sheath 18. Then, the axial electrode 24 is housed inside the sheath 18 and thereby enters a non-exposed state. Accordingly, when a high frequency current is applied, cleavage or dissection is not performed by the axial electrode 24, and cleavage is performed only by the conductive portion 34 that is exposed in a band shape on the lateral face of the distal end electrode portion 12.

Next, an example of a surgical method for performing endoscopic submucosal dissection using the above described treatment instrument 10 for an endoscope is described based on FIGS. 4A to 4G. The example hereunder describes a technique in a case that a lesion 42A is present in the mucosa 42, and the lesion 42A is removed without damaging the muscularis propria 32 in a subject body shown in FIG. 5. Since the treatment instrument 10 for an endoscope according to this embodiment is a mono-polar type treatment instrument in which only one electrode is provided at the distal end electrode portion 12, another electrode (counter electrode plate) is previously attached to the subject body before the treatment.

First, the surgeon confirms the lesion 42A on a display (not shown) by means of an observation optical system (reference numeral 45 in FIG. 12) provided in an endoscope insertion portion 44. At that time, the surgeon may stain the lesion 42A by pouring a dye such as indigo carmine on the lesion 42A from a nozzle of the endoscope insertion portion 44.

Next, as shown in FIG. 4A, markings 46, 46 . . . are made at predetermined intervals around the lesion 42A. The method of making the markings 46, 46 . . . is not particularly limited. For example, cauterization is performed in a spot-like manner using a high-frequency knife 48 that has an acicular distal end. The high-frequency knife 48 is a treatment instrument in which a thin metal conducting wire is inserted through the inside of an insulating tube, and a distal end of the metal conducting wire protrudes by a predetermined length from the distal end of the insulating tube. The protruding portion of the metal conducting wire serves as an electrode so that an inner wall of the body is dissected or resected by a high frequency current that flows to the wire.

Next, as shown in FIG. 4B, an injection needle 50 is inserted through the forceps channel of the endoscope insertion portion 44 and led out from the distal end of the endoscope insertion portion 44. Then, a drug solution is locally injected (a localized injection) into submucosa 52 (see FIG. 5) around the lesion 42A by the injection needle 50. Physiological saline is generally used as the drug solution, and hyaluronate sodium that has high viscosity may also be used. By performing the localized injection in the entire area surrounding the lesion 42A in this manner, the entire lesion 42A enters a state in which it protrudes significantly.

Subsequently, the injection needle 50 is drawn out from the forceps channel of the endoscope insertion portion 44, and the high-frequency knife 48 is re-inserted through the forceps channel. Next, as shown in FIG. 4C, precutting is performed with the high-frequency knife 48 to form an opening portion 54 that is larger than the distal end electrode portion 12 in the mucosa 42. The opening portion 54 may also be formed in the vicinity of the markings when forming the markings in FIG. 4A.

Figure 5:
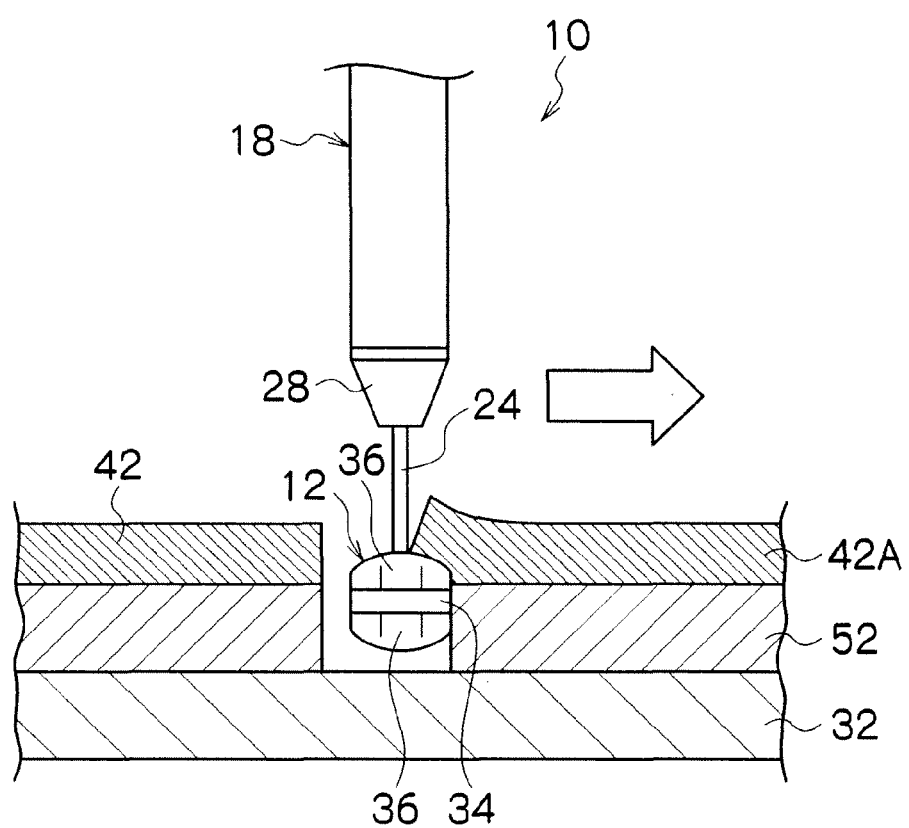
FIG. 5 is an view that illustrates a state in which mucosa is dissected by an axial electrode of the treatment instrument for an endoscope according to the embodiment.

Next, the high-frequency knife 48 is drawn out from the forceps channel of the endoscope insertion portion 44. Thereafter, the treatment instrument 10 for an endoscope of the present embodiment is inserted through the forceps channel. Then, as shown in FIG. 4D, the distal end electrode portion 12 is led out from the distal end of the endoscope insertion portion 44. After exposing the axial electrode 24 from the distal end of the endoscope insertion portion 44, the distal end electrode portion 12 is inserted into the opening portion 54 of the mucosa 42, and the distal end electrode portion 12 is slipped into the submucosa 52 as shown in FIG. 5. At this time, the distal end electrode portion 12 can be made to approach a digestive tract wall from a vertical direction. Accordingly, the distal end electrode portion 12 can be made to approach the digestive tract wall without changing the posture of the endoscope insertion portion 44. An operation to expose the axial electrode 24 may also be performed after the distal end electrode portion 12 has been slipped into the submucosa 52.

Subsequently, while passing a high frequency current to the axial electrode 24, as shown in FIG. 4E, the distal end electrode portion 12 is moved in a lateral direction (that is, parallel to the muscularis propria) along the markings 46, 46 . . . . As a result, since the axial electrode 24 that is in the exposed state contacts against the mucosa 42, the mucosa 42 around the lesion 42A is dissected by the axial electrode 24 that is in the exposed state. At this time, the lesion 42A of the mucosa 42 can be cleaved by merely moving the distal end electrode portion 12 in a lateral direction, without changing a posture of the distal end electrode portion 12. Further, at this time, since a high frequency current is also passed to the conductive portion 34 that is exposed in a band shape on the side face of the distal end electrode portion 12, it is possible to cleave the submucosa 52 at the same time as performing dissection of the mucosa 42. Furthermore, since the non-conductive portion 36 is provided on the distal end side of the distal end electrode portion 12, the mucosa 42 and the submucosa 52 can be safely cleaved without damaging the muscularis propria 32.

Figure 6:
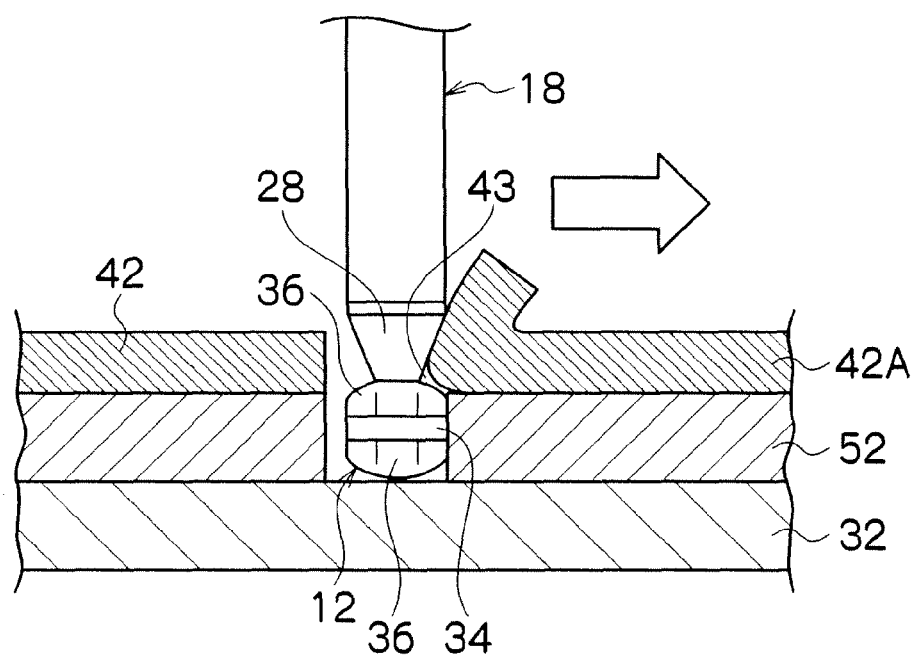
FIG. 6 is an view that illustrates a state in which submucosa is resected by the distal end electrode portion of the treatment instrument for an endoscope according to the embodiment.

After dissecting the lesion 42A, the axial electrode 24 is retracted into the sheath 18. Subsequently, in a state in which a high frequency current is passed to the conductive portion 34 of the distal end electrode portion 12, the distal end electrode portion 12 is moved laterally (to the center side of the lesion 42A) while pushing the distal end of the distal end electrode portion 12 against the muscularis propria 32 as shown in FIG. 6. As a result, since the conductive portion 34 that is exposed at the lateral face of the distal end electrode portion 12 contacts against the submucosa 52, the contacted submucosa 52 is cleaved. At this time, since the non-conductive portion 36 is disposed between the conductive portion 34 and the muscularis propria 32, the conductive portion 34 moves at a position that is separated from the muscularis propria 32 by the amount of the thickness of the non-conductive portion 36. Therefore, it is possible to prevent the conductive portion 34 from contacting against the muscularis propria 32 and cleaving the muscularis propria 32.

By moving the distal end electrode portion 12 to the center side of the dissection portion, as shown in FIG. 4F, the lesion 42A is gradually ablated from the submucosa 52. By repeating this operation, as shown in FIG. 4G, the lesion 42A can be completely cut off. The lesion 42A that has been cut off can be taken out by inserting a treatment instrument such as a forceps into the forceps channel of the endoscope insertion portion 44, and grasping the lesion 42A with the treatment instrument.

The distal end portion of the collar member 28 that is the distal end portion of the sheath 18 is formed in a tapered shape. The diameter of the distal end side of the exposed portion is smaller than the diameter of the proximal end side (the tube side) of the exposed portion.

Figure 7A:
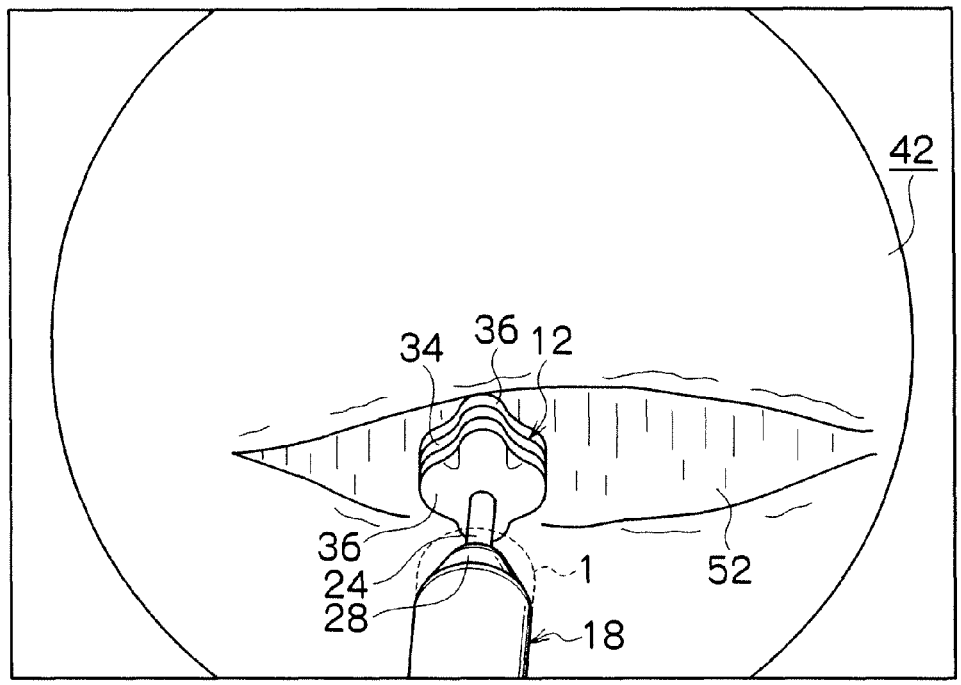
FIGS. 7A and 7B are views of the treatment instrument for an endoscope according to the embodiment, the treatment instrument that is in an observation field of view range.
Figure 7B:
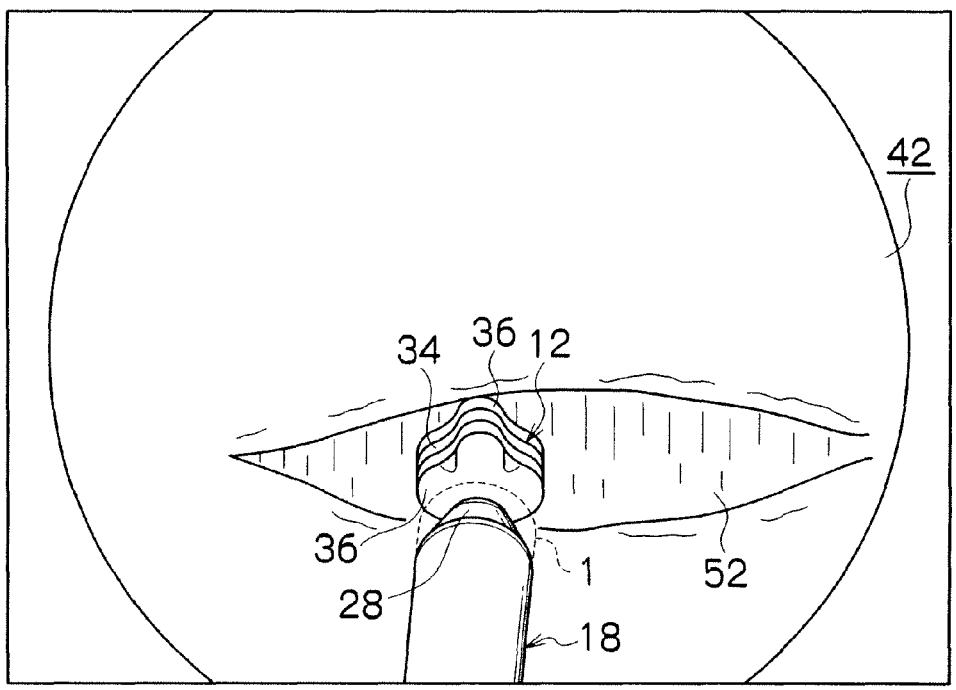

The distal end portion of the sheath 18 is formed in a tapered shape, as shown in FIGS. 7A and 7B, and therefore, a part of the distal end portion (the collar member 28) of the sheath 18 that appears in the observation image shown inside the frame becomes reduced in size. The broken lines in FIGS. 7A and 7B show the external shape of a conventional sheath 1 that merely has a circular cylindrical shape. According to the sheath 1, when performing the dissection as shown in FIG. 7A, in a state in which the axial electrode 24 is caused to protrude, the proximal end portion side of the axial electrode 24 hides behind the sheath 1 and cannot be observed because a view of the axial electrode 24 is blocked by the distal end portion of the sheath 1. In contrast, according to the sheath 18 of the present embodiment indicated by the solid lines, since the distal end portion is formed in a tapered shape, the entire axial electrode 24 including the proximal end portion of the axial electrode 24 can be observed.

Figure 12:
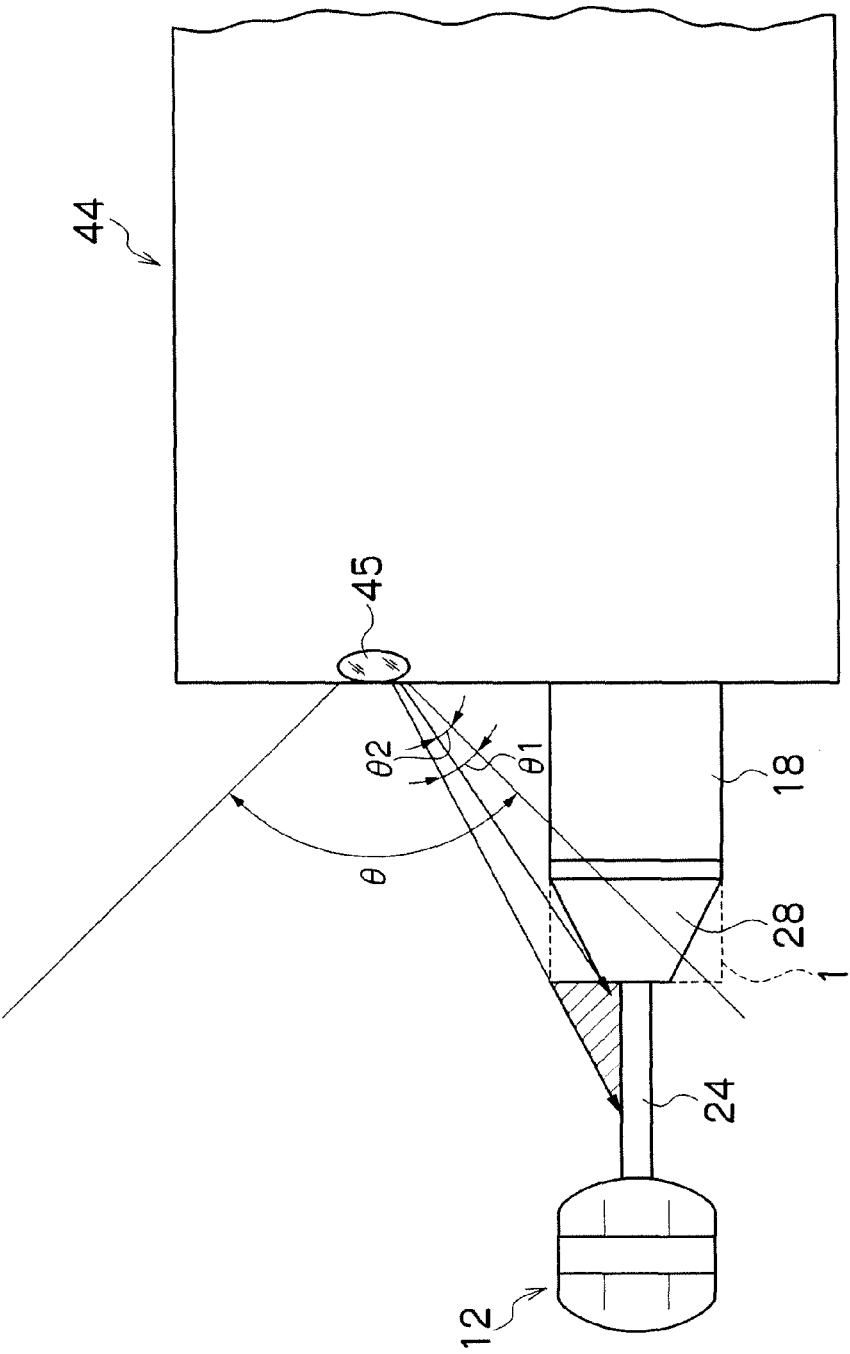
FIG. 12 is a side view that illustrates a proximity of the distal end of the insertion portion of the endoscope corresponding to FIG. 7A.

FIG. 12 is a side view that illustrates proximity of the distal end of the insertion portion 44 of the endoscope corresponding to FIG. 7A. As shown in FIG. 12, a distal end portion of the sheath 18 protrudes from the forceps channel at a distal end of the insertion portion 44 of the endoscope, and the axial electrode 24 protrudes from the distal end portion of the sheath 18.

As shown in FIG. 12, a view angle θ of the observation optical system 45 included in the insertion portion 44 of the endoscope along vertical direction (longitudinal direction) is about 90 degree or more and about 100 degree or less. Either the conventional sheath 1 which has a circular cylindrical shape and is indicated by the broken line or the sheath 18 of the present embodiment which has the distal end portion formed in a tapered shape and is indicated by the solid lines blocks a bottom part of the visual field of the observation optical system 45. However, a view angle $θ_1$ indicating a size of a blocked area blocked by the circular cylindrically-shaped sheath 1 is larger than a view angle $θ_2$ indicating a size of a blocked area blocked by the sheath 18 of the present embodiment. Therefore, according to the present embodiment, the entire portion of the distal end of the treatment instrument 10 for an endoscope including the proximal end of the axial electrode 24 can be observed.

FIG. 7B shows a state in which the axial electrode 24 has been retracted into the sheath 18 at a time of resection. The conductive portion 34 of the distal end electrode portion 12 is exposed around the circumference of the lateral face of the distal end electrode portion 12. In this state, according to the sheath 1 indicated by the broken line, although the submucosa 52 that contacts against the conductive portion 34 is resected, about ⅓ of the area of the lower side of the distal end electrode portion 12 hides behind the sheath 1 and cannot be observed because a view of the distal end electrode portion 12 is blocked by the distal end portion of the sheath 1. In contrast, with the sheath 18 of the present embodiment indicated by the solid lines, since the distal end portion of the sheath 18 is formed in a tapered shape, the portion that is hidden by the distal end electrode portion 12 and cannot be observed is reduced to ¼ or less of the area of the lower side of the distal end electrode portion 12.

Thus, according to the sheath 18 of the present embodiment, the distal end electrode portion 12, the axial electrode 24, and dissection or resection treatment site or the like can be observed. The thickness of mucosa 42 or submucosa 52 that is dissected or resected by ESD is extremely thin. In the esophagus, the thickness is approximately 0.5 to 0.8 mm for the mucosa 42 and approximately 0.3 to 0.7 mm for the submucosa 52. In the stomach, the thickness is approximately one to several mm. Therefore, although safety is ensured by forming the distal end electrode 12 in a sandwich structure and the like, it is extremely important to observe the treatment site with certainty. According to the treatment instrument 10 for an endoscope of the present embodiment, visibility with respect to the distal end electrode portion 12, the axial electrode 24, and the treatment site can be improved, and the ESD safety can be ensured.

Further, the distal end portion of the sheath 18 is formed in a tapered shape. Thus, when shifting from a state in which the axial electrode 24 protrudes (state of dissecting circumference of the mucosa 42 using the axial electrode 24; see FIG. 5) to a state in which the axial electrode 24 is retracted into the sheath 18 (state in which the submucosa 52 is ablated using the distal end electrode portion 12; see FIG. 6), and causing the distal end portion of the sheath 18 to advance towards the inside of the mucosa 42 (submucosa 52), the distal end portion of the sheath 18 can be easily advanced into the mucosa 42 (submucosa 52).

Further, in a state in which the submucosa 52 is ablated (see FIG. 4F and FIG. 6), depending on the state of the ablated mucosa 42 or submucosa 52, where appropriate, the distal end electrode portion 12 that has been slipped into the submucosa can be drawn out and, after changing the location or posture of the distal end electrode portion 12, slipped into the submucosa again to proceed the ablation. In such case, for example, when the outer diameter of the sheath 18 and the outer diameter of the distal end electrode portion 12 are approximately equal, in a state in which the axial electrode 24 is retracted, it is difficult to slip the distal end electrode portion 12 under the mucosa 42 when the dissected and ablated mucosa 42 is not turned up by 90 degrees or more in a state in which the mucosa 42 is rolled up. Furthermore, it is difficult to bring the conductive portion 34 of the distal end electrode portion 12 into contact against fiber of the submucosa 52 under the mucosa 42 that the surgeon is attempting to ablate. However, by forming the distal end portion of the sheath 18 in a tapered shape, even in a state in which the ablated mucosa is only turned up at an angle that is less than 90 degrees, it is possible to easily slip the distal end electrode portion 12 or the distal end portion of the sheath 18 under the mucosa 42. Accordingly, it is possible to easily contact the conductive portion 34 of the distal end electrode portion 12 against the fiber of the submucosa 52, and ablate the submucosa 52 safely and with ease.

Further, when moving the distal end electrode portion 12 in a lateral direction to perform dissection or ablation of the submucosa 52, the conventional sheath 1 that merely has a cylindrical shape has the problem that the mucosa 42 becomes entwined around the distal end portion of the sheath 1, and it is difficult to view the distal end electrode portion 12 or the treatment site due to the entwined mucosa 42. However, according to the sheath 18 of the present embodiment, the mucosa 42 that contacts against the tapered portion of the distal end portion of the sheath 18 is guided by the tapered face of the tapered portion so as to be turned outward as illustrated in FIG. 6. It is easy to observe the distal end electrode portion 12 or the treatment site, and the visibility with respect to the distal end electrode portion 12 or the treatment site is further improved.

Figure 13:
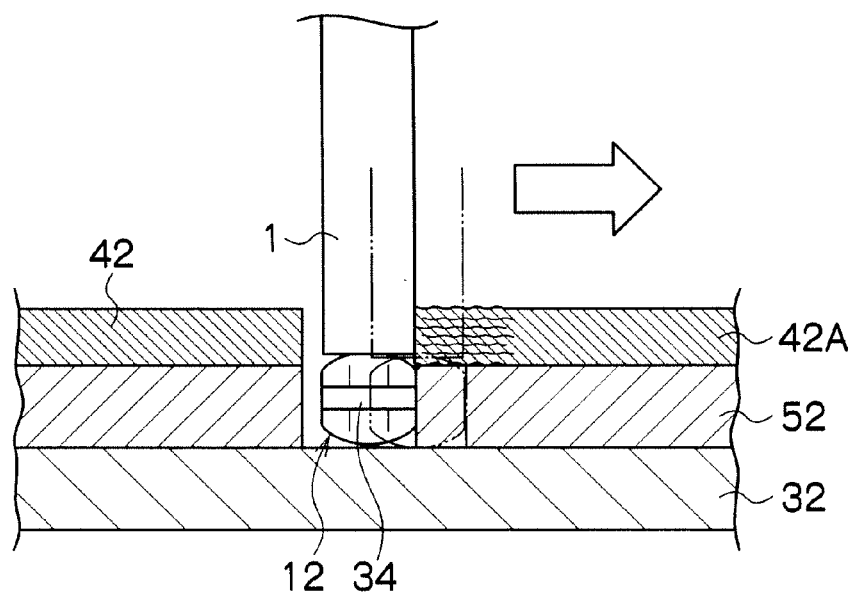
FIG. 13 is a view that illustrates a state that a lateral face of a conventional sheath comes into contact with a marginal part of a lesion.

Incidentally, when an operation for dissecting and ablating the submucosa 52 by the conductive portion 34 is started by moving the distal end electrode portion 12 along a lateral direction, when using the circular cylindrically-shaped sheath 1, a marginal part of the lesion 42A comes into contact with the lateral face of the sheath 1, as shown in FIG. 13. Then, when the distal end electrode portion 12 is moved a more long distance along the lateral direction, the distal end electrode portion 12 can be moved to a certain degree along the lateral direction since the lesion 42A changes its shape. However, since a reaction force by an end portion of the lesion 42A increases with a lateral movement of the distal end electrode portion 12, the lateral movement of the distal end electrode portion 12 is prevented by the reaction force. Thus, it is impossible to perform the operation for dissecting and ablating the submucosa 52 by using the conventional sheath 1 smoothly.

On the contrary, the sheath 18 of the present embodiment shown in FIG. 6 includes the collar member 28 which has a tapered face, therefore an allowance space (back clearance) 43 is provided between the distal end portion of the sheath 18 (except the collar member 28) and the distal end electrode portion 12. The allowance space 43 and the collar member 28 achieve an operation and an effect described below.

More specifically, when an operation for dissecting and ablating the submucosa 52 by the conductive portion 34 is started by moving the distal end electrode portion 12 along a lateral direction, the marginal part of the lesion 42A passes the allowance space 43 and comes into contact with the tapered face of the collar member 28. Then, when the distal end electrode portion 12 is moved a more long distance along the lateral direction, the end portion of the lesion 42A is guided by the tapered face of the collar member 28 to be rolled up away from the collar member 28. Since the end portion of the lesion 42A is rolled up, the reaction force by the end portion of the lesion 42A applied to the distal end electrode portion 12 is reduced (minimized). Thus, the distal end electrode portion 12 can move along the lateral direction smoothly. Therefore, it is possible to perform the operation for dissecting and ablating the submucosa 52 by the conductive portion 34 smoothly. As described above, the allowance space 43 is provided for the treatment instrument 10 for an endoscope, and the tapered face of the collar member 28 is included in the treatment instrument 10 for an endoscope. Therefore the effect that the end portion of the lesion 42A is rolled up away from the collar member 28 smoothly is achieved. The size of the allowance space 43 is arbitrarily configured by changing an angle of the tapered face of the collar member 28. The size of the allowance space 43 is preferably large rather than small.

Furthermore, the arc shape of the corner portion of the distal end electrode portion 12 also contributes considerably to the operation that turns up the mucosa 42.

It should be understood that the term "tapered portion of the distal end portion of the sheath 18" in the present embodiment also refers to a portion that is formed in a tapered shape with a continuous surface, or in a shape that is tapered in a stepwise fashion.

Figure 8A:
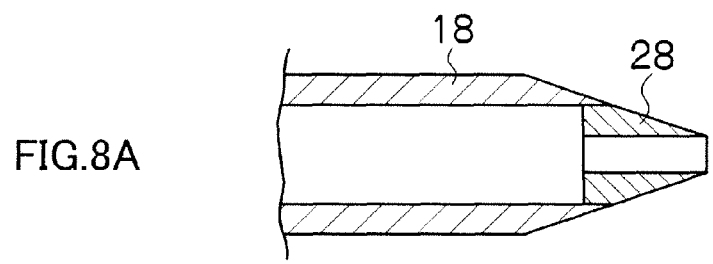
FIGS. 8A to 8E are structural views that illustrate embodiments of the structure of a distal end portion of a sheath of the treatment instrument for an endoscope.
Figure 8B:
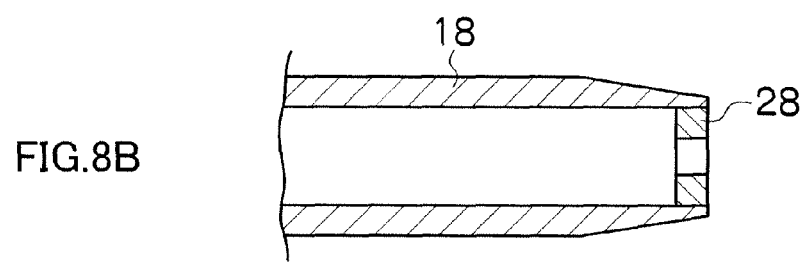
Figure 8C:
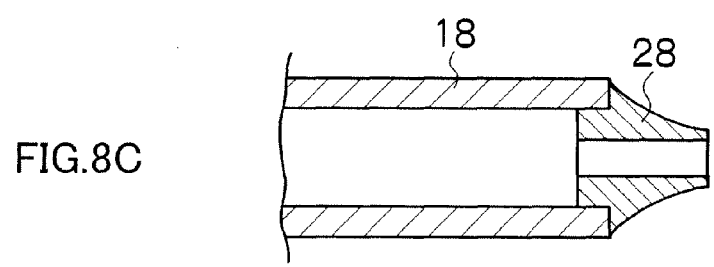
Figure 8D:
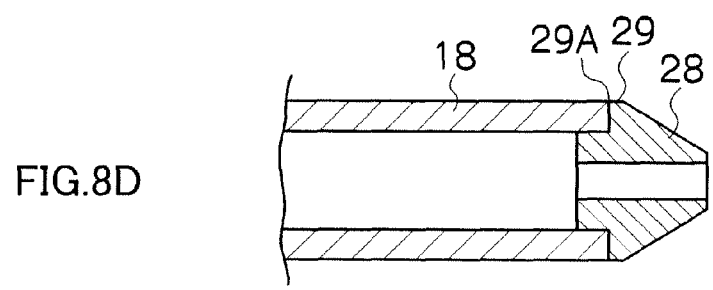
Figure 8E:
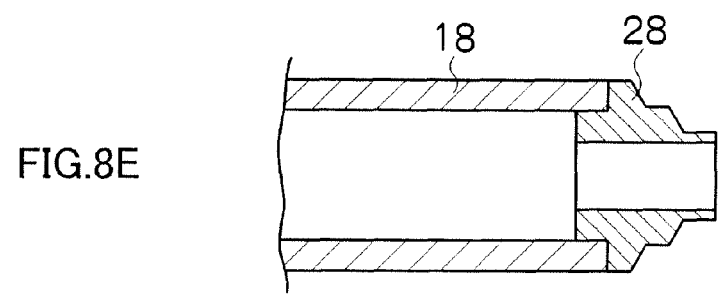

For example, as shown in FIG. 8A, a configuration may be adopted in which both the distal end portion of the sheath 18 and the distal end portion of the collar member 28 have a cross section that is a continuous linear tapered face. Further, as shown in FIG. 8B, a configuration may be adopted in which a cross section of only the distal end portion of the sheath 18 is a continuous linear tapered face. Furthermore, as shown in FIG. 8C, a configuration may be adopted in which only the collar member 28 is provided with an arcuate tapered face. Further, as shown in FIG. 8D, a configuration may be adopted in which a cross section of only the collar member 28 is a continuous linear tapered face. In the example shown in FIG. 8D, a flat end face 29 is formed around the circumference of the collar member 28 so as to be flush with the outer circumferential face of the sheath 18. In a case in which the end face 29 protrudes from the outer circumferential face of the sheath 18 due to a dimensional error or the like, since the angle of a corner portion 29A on the proximal end portion side of the end face 29 is approximately 90 degrees and is not an acute angle, damage to tissue or the like inside a body cavity due to the corner portion 29A catching on the tissue or the like can be suppressed. Further, as shown in FIG. 8E, a configuration may be adopted in which the collar member 28 is formed in a stepped shape as a tapered face. More specifically, the term "tapered portion" according to this embodiment includes all shapes that are formed in a shape that the diameter of the distal end side of the exposed portion is smaller than the diameter of the proximal end side (the tube side) of the exposed portion.

According to the treatment instrument 10 for an endoscope of the present embodiment, the tapered portion of the distal end portion of the sheath 18 includes the collar member 28 made of ceramic that is a separate element to the sheath 18, and the collar member 28 is attached to the distal end opening portion of the sheath 18. The axial electrode 24 is slidably supported in the through-hole 28A formed with a ceramic, which has high rigidity. Therefore, an operation to cause the axial electrode 24 to protrude or retract is stable and, further, wobbling of the axial electrode 24 or the distal end electrode 12 when performing dissection or resection is suppressed. Thus, the operability of the treatment instrument 10 for an endoscope is improved.

In the distal end electrode portion 12 of the treatment instrument 10 for an endoscope of the present embodiment, the lateral face of the distal end electrode portion 12 is formed in a sandwich structure in which the band-shaped conductive portion 34 is sandwiched between the non-conductive portions 36 and 36. Hence, when the distal end of the distal end electrode portion 12 is contacted against the muscularis propria 32, the non-conductive portion 36 contacts against the muscularis propria 32, and the conductive portion 34 does not contact against the muscularis propria 32. Accordingly, cleaving of the muscularis propria 32 can be reliably prevented. Further, according to the distal end electrode portion 12 of the embodiment, by moving the distal end electrode portion 12 in a lateral direction, the lateral face of the distal end electrode portion 12 contacts against the submucosa 52, and the submucosa 52 that contacts against the band-shaped conductive portion 34 is cleaved. Therefore, according to the distal end electrode portion 12, the submucosa 52 can be cleaved without damaging the muscularis propria 32.

Figure 9:
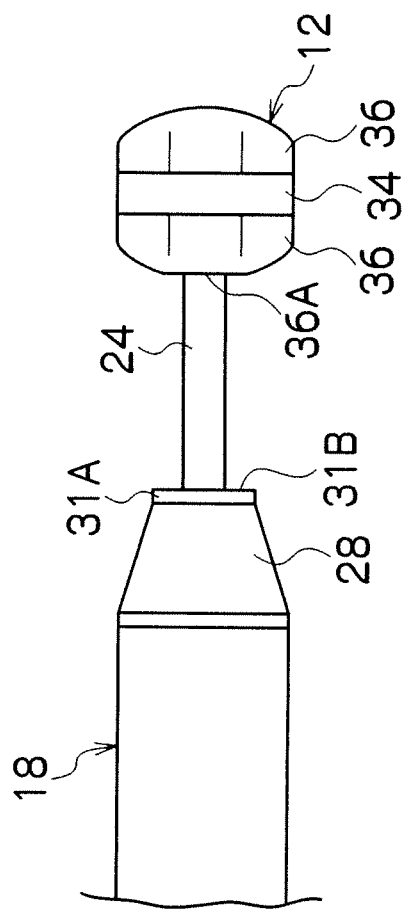
FIG. 9 is a side view that shows the second embodiment of the treatment instrument for an endoscope.

FIG. 9 is a side view that illustrates a treatment instrument for an endoscope according to the second embodiment. In FIG. 9, members that are the same as, or similar to, members of the treatment instrument 10 for an endoscope shown in FIG. 3 are designated by the same reference numerals, and a description of those members is omitted.

In the treatment instrument for an endoscope shown in FIG. 9, a flat face 31A that is substantially parallel with the protrusion/retraction direction of the axial electrode 24 is formed at the distal end portion of the sheath 18, that is, at the distal end portion of the collar member 28, and an end face 31B of the flat face 31A is formed in a largish fashion. When the axial electrode 24 is retracted into the sheath 18, a rear end face 36A of the non-conductive portion 36 on the proximal end side of the distal end electrode portion 12 has surface contact with the end face 31B. Therefore, the distal end electrode portion 12 is stably retained by the end face 31A of the collar member 28. Further, since an inclination angle of the tapered portion is increased by forming the flat face 31A in the collar member 28, an even wider field of view can be secured. A length in the axial direction of the collar member 28 that protrudes from the sheath 18 is decided based on the viewpoint of stably supporting the axial electrode 24. Since a large inclination angle can be provided for the tapered portion by forming the flat face 31A within the decided length, the flat face 31A can contribute to improving the degree to which the field of view is secured.

Although according to the above described embodiments the distal end electrode portion 12 is formed in a substantially gear-wheel shape, the shape or configuration of the distal end electrode portion 12 is not limited to the above described embodiment, and various forms thereof are possible.

Figure 10:
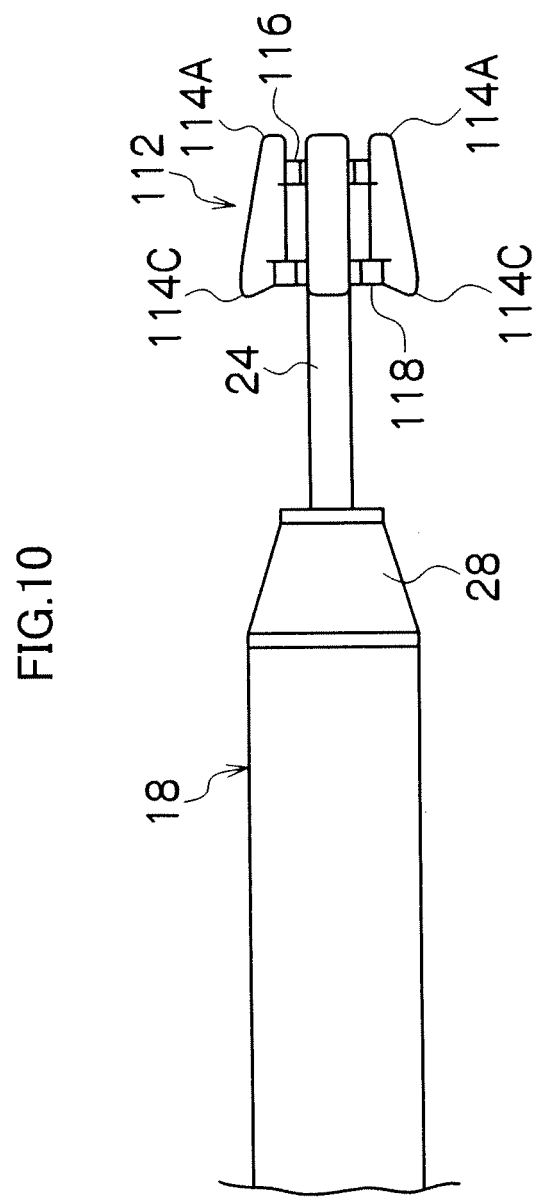
FIG. 10 is a side view that shows the third embodiment of the treatment instrument for an endoscope.
Figure 11:
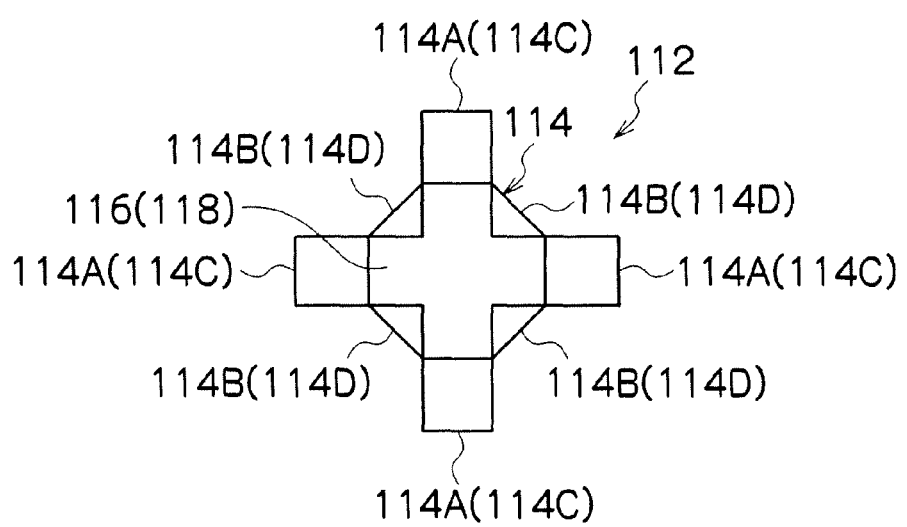
FIG. 11 is a front view of a distal end electrode portion of the treatment instrument for an endoscope shown in FIG. 10.

For example, a distal end electrode portion 112 shown in FIG. 10 and FIG. 11 which show the third embodiment is formed in a shape in which four plate members are combined in the shape of a cross. More specifically, in a main unit 114 of the distal end electrode portion 112, four non-conductive plate members are disposed at 90° intervals to form a cross shape that connects with a central shaft side of the distal end electrode portion 114.

On the distal end side of the main unit 114, four protruded portions 114A, 114A, . . . are formed by each plate member protruding to the distal end side, and depressed portions 114B, 114B, . . . are formed at center positions between each of the protruded portions 114A, 114A, . . . . Similarly, on the proximal end side of the main unit 114, protruded portions 114C, 114C, . . . are formed by each plate member protruding to the proximal end side, and depressed portions 114D, 114D, . . . are formed at center positions between each of the protruded portions 114C, 114C, . . . .

A cross-shaped electrode plate 116 is provided in the depressed portions 114B, 114B . . . on the distal end side. The electrode plate 116 is arranged at a position that is away from the top of the protruded portions 114A, 114A, . . . so that the electrode plate 116 does not come in contact with the muscularis propria 32 even when the protruded portions 114A, 114A, . . . come in contact with the muscularis propria 32. Likewise, a cross-shaped electrode plate 118 is also provided in the depressed portions 114D, 114D, . . . on the proximal end side. The electrode plate 118 is arranged at a position that is away from the distal end of the protruded portions 114C, 114C, . . . . The two electrode plates 116 and 118 are connected to the axial electrode 24.

The entire main unit 114 is formed so that the distal end side is smaller than the proximal end side thereof. Further, the size of the protruded portions 114A, 114A, . . . , and 114C, 114C, . . . decreases in accordance with the closeness of the protruded portion to the distal end side, and the distal end of each protruded portion is roundly formed so as to have a non-dissecting property. Accordingly, the main unit 114 is configured such that the main unit 114 can be easily pushed into the fibrous submucosa 52, and that the protruded portions 114A, 114A, . . . do not damage the muscularis propria 32. The size of the main unit 114 is substantially smaller than the inner dimensions of the forceps channels of the endoscope, and is such that the main unit 114 can pass through the forceps channel of the endoscope unhindered.

With the treatment instrument for an endoscope configured in this manner, it is possible to perform a pushing and cutting operation in which the distal end electrode portion 112 cleaves the submucosa 52 while advancing the distal end electrode portion 112 to the distal end side, and a pulling and cutting operation in which the distal end electrode portion 112 cleaves the submucosa 52 while the distal end electrode portion 112 is pulled back to the proximal end side. Further, according to this treatment instrument for an endoscope, the electrode plates 116 and 118 are arranged at a center position of the distal end electrode portion 112. Therefore, even when the distal end electrode portion 112 is rotated around the axis line, the electrode plates 116 and 118 are always at the center position. Accordingly, cleavage of the submucosa 52 can be performed without affecting the posture of the distal end electrode portion 112.

In the treatment instrument for an endoscope of the third embodiment, the distal end portion of the sheath 18 is formed in a tapered shape. Therefore, it is possible to prevent the axial electrode 24 or a treatment site from being hidden behind the distal end of the sheath 18. Further, since it is easy to slip the distal end electrode portion 112 into a region under the mucosa 42, visibility and operability are significantly improved.

Although according to the third embodiment the main unit 114 is formed by combining four plate-shaped members, the number of plate-shaped members may be three or less, or five or more. In either case, it is preferable that the plate-shaped members are spaced at equal angles.

Further, according to the treatment instrument 10 for an endoscope of the above described embodiments, with respect to the tapered portion of the distal end portion of the sheath 18, it is preferable to satisfy a requirement described by expressions: $0.5a \leq b \leq 1.5a$, $0.4c \leq d \leq 0.6c$, and $d<b$, as shown in FIG. 3, where the external dimensions of the distal end electrode portion 12 are denoted by "a", the length in the axial direction of the tapered portion is denoted by "b", the external dimensions on the proximal end side of the tapered portion is denoted by "c", and the external dimensions on the distal end side of the tapered portion are denoted by "d".

Japanese Patent Publication No. 3655664 discloses a high-frequency knife having a flexible pipe formed in a tapered shape in which a distal end portion of the flexible pipe is turned inward. However, because the size of the tapered portion of the flexible pipe is too small as a tapered portion for improving visibility, it is not possible to achieve the effects of the embodiments of the present invention.

Therefore, as to the size of the tapered portion of the embodiment of the present invention, it is preferable to satisfy the requirement described by the expressions: $0.5a \leq b \leq 1.5a$, $0.4c \leq d \leq 0.6c$, and $d<b$, where the external dimensions of the distal end electrode portion 12 are denoted by "a", the length in the axial direction of the tapered portion is denoted by "b", the external dimensions on the proximal end side of the tapered portion is denoted by "c", and the external dimensions on the distal end side of the tapered portion are denoted by "d".

When the length "b" is less than 0.5a, the tapered portion resembles the tapered portion disclosed in Japanese Patent Publication No. 3655664, and visibility can not be secured. Further, when the length "b" exceeds 1.5a, since the rigidity of the distal end portion decreases, the insertability of the endoscope insertion portion 44 with respect to the forceps channel deteriorates. Hence, the length "b" is preferably decided such that $0.5a \leq b \leq 1.5a$, and more preferably $0.6a \leq b \leq 1.2a$.

Further, when the length "b" in the axial direction of the tapered portion is less than 0.5a, it is not possible to secure the field of view and it is also difficult to slip the distal end electrode 12 into the submucosa 52 from ablated mucosa 42A. Further, when the length "b" in the axial direction of the tapered portion exceeds 1.5a, the tapered portion becomes too long. Therefore the length of the axial electrode (retracted state) 24 positioned inside the sheath 18 also increases, and a rigid section (guide portion of axial electrode 24) at the distal end of the sheath 18 lengthens. As a result, the insertability of the treatment instrument 10 for an endoscope into the forceps channel deteriorates.

With regard to the external dimensions "d" on the distal end side of the tapered portion, ideally the external dimensions "d" should be close to the diameter of the axial electrode 24. Since the external dimensions "d" are too small when they are less than 0.4c, the diameter of the axial electrode 24 also narrows and there is a risk of the axial electrode 24 breaking. Further, in this case, since the distal end becomes too sharp, there is a risk of damaging the mucosa 42 or the submucosa 52. Furthermore, since the distal end contacts against the proximal end of the distal end electrode portion 12 when the axial electrode 24 is in a retracted state, the stability of the distal end electrode portion 12 deteriorates. When the external dimensions "d" on the distal end side of the tapered portion is larger than 0.6c, the angle of the tapered portion becomes obtuse, and the field of view can not be secured because the shape of the tapered portion approaches a circular cylindrical shape. The expression d<b is a conditional expression for clarifying that the tapered portion is not chamfered.

Although the above embodiments are described using an example of a monopolar-type device in which one electrode is provided in the distal end electrode portions 12 and 112, the present invention may also be applied to a bipolar type device in which both electrodes are provided in the distal end electrode portions 12 and 112.

What is claimed is:

1. A treatment instrument for an endoscope, said treatment instrument comprising:
   an operation portion;
   a cylindrical sheath that is connected to the operation portion and that also comprises an insertion portion;
   an axial electrode that protrudes from and retracts into a distal end opening portion of the sheath by an operation of the operation portion; and
   a distal end electrode portion that is provided at a distal end portion of the axial electrode;
   wherein a distal end portion of the sheath includes a tapered portion, the tapered portion being formed in a tapered shape such that a distal end side of the distal end portion is narrower than a proximal end side of the distal end portion, and
   wherein the tapered portion of the distal end portion of the sheath is formed to satisfy a condition indicated by expression: $0.4c \leq d \leq 0.6c$, where an external diameter on the proximal end side of the tapered portion is denoted by "c", and an external diameter on the distal end side of the tapered portion is denoted by "d".

2. The treatment instrument for an endoscope according to claim 1, wherein the tapered portion of the distal end portion of the sheath is formed in the tapered shape with a continuous surface, or in a shape that is tapered in a stepwise fashion.

3. The treatment instrument for an endoscope according to claim 1, wherein the tapered portion of the distal end portion of the sheath comprises an insulative member that is a separate element from the sheath, and the insulative member is attached to the distal end opening portion of the sheath.

4. The treatment instrument for an endoscope according to claim 1, wherein the distal end electrode portion includes:
   a conductive portion; and
   non-conductive portions which is provided on a distal end side and a proximal end side of the conductive portion, and sandwiches the conductive portion, and
   wherein the conductive portion exposes in a band shape on a lateral face of the distal end electrode portion.

5. The treatment instrument for an endoscope according to claim 1, wherein the distal end electrode portion comprises:
   an non-conductive portion that is formed in a cross shape; and
   conductive portions that are provided at a distal end side and a proximal end side of the non-conductive portion.

6. The treatment instrument for an endoscope according to claim 1, wherein the tapered portion of the distal end portion of the sheath is formed to satisfy a condition indicated by expressions: $0.5a \leq b \leq 1.5a$, and d<b, where a length in an axial direction of the distal end electrode portion is denoted by "a", and a length in an axial direction of the tapered portion is denoted by "b".

7. The treatment instrument for an endoscope according to claim 1, wherein the tapered portion comprises a flat end face formed around a circumference of the tapered portion that is flush with an outer circumferential face of the sheath.

8. The treatment instrument for an endoscope according to claim 1, wherein an external diameter of the tapered portion continuously decreases from the proximal end side of the tapered portion to the distal end side of the tapered portion.

9. The treatment instrument for an endoscope according to claim 1, wherein the distal end portion of the sheath and the distal side of the tapered portion include a continuous linear tapered face cross section.

10. The treatment instrument for an endoscope according to claim 1, wherein the distal end portion of the sheath includes a continuous linear tapered face cross section.

11. The treatment instrument for an endoscope according to claim 1, wherein the tapered portion of the distal end portion of the sheath is formed to satisfy a condition indicated by expression: $0.5a \leq b \leq 1.5a$, where a length in an axial direction of the distal end electrode portion is denoted by "a", and a length in an axial direction of the tapered portion is denoted by "b".

* * * * *